United States Patent [19]

Yoshioka et al.

[11] Patent Number: 5,034,558

[45] Date of Patent: Jul. 23, 1991

[54] PROCESS FOR PURIFYING METHYL METHACRYLATE

[75] Inventors: Teruhiko Yoshioka, Otake; Kouhei Okamura, Yanai; Masao Kobayashi, Hiroshima, all of Japan

[73] Assignee: Mitsubishi Rayon Co., Ltd., Tokyo, Japan

[21] Appl. No.: 364,508

[22] Filed: Jun. 9, 1989

Related U.S. Application Data

[63] Continuation-in-part of Ser. No. 353,437, May 18, 1989, abandoned.

[30] Foreign Application Priority Data

May 25, 1988 [JP] Japan ................... 63-127952

[51] Int. Cl.[5] .............................. C07C 67/48
[52] U.S. Cl. .................................... 560/218
[58] Field of Search .......................... 560/218

[56] References Cited

U.S. PATENT DOCUMENTS 4,625,059 11/1986 Shibano et al. ................. 562/600

FOREIGN PATENT DOCUMENTS 52-23017 2/1977 Japan .
58-183641 10/1983 Japan .
63-2952 7/1988 Japan .

*Primary Examiner*—Paul J. Killos
*Attorney, Agent, or Firm*—Armstrong, Nikaido, Marmelstein, Kubovcik & Murray

[57] ABSTRACT

A process for purifying methyl methacrylate which comprises treating methyl methacrylate having a purity of 99.5% or more containing a trace of impurities with a sulfonic acid group-containing compounds. According to the present invention, there can be obtained highly purified methyl methacrylate which exhibits an absorbance of 0.02 or less in a range of wavelength of 400–500 nm according to the sulfuric acid color method and is free of even a trace of furan-type compounds.

13 Claims, No Drawings

PROCESS FOR PURIFYING METHYL METHACRYLATE

This application is a continuation-in-part of application Ser. No. 353,437 filed May 18, 1989, abandoned.

The present invention relates to a process for purifying methyl methacrylate and to a methyl methacrylate monomer purified by the same process. More particularly, the present invention relates to a process for purifying methyl methacrylate which comprises treating methyl methacrylate having a purity of 99.5% or more containing, as small traces of impurities, furan-type compounds such as furfural, 2,5-dimethylfuran, 5-methylfurfural, protoanemonin and the like (the above methyl methacrylate being hereinafter referred to as the MMA), with one or more sulfonic a sulfonic acid group-containing compounds, thereby removing the larger part of said impurities from the MMA, and the methyl methacrylate that is purified by said process.

Therefore proposed as processes for purifying methyl methacrylate were (1) removing organic acids or methanol as impurities by washing it with water;
(2) removing impurities by rectifying it;
(3) removing impurities by distilling it together with a polyamine (Japanese Patent Application Kokai No. 52-23017);
(4) removing a trace of organic acids with a weakly basic anion exchange resin (Japanese Patent Application Kokai No. 63-2952); and the like.

Although, however, the purity of the methyl methacrylate obtained by the above processes is sufficient for ordinary uses, it is still insufficient for the material for electronic devices, optical materials and the like requiring a particularly high purity. Attention has rarely been paid to removing furan-type compounds such as furfural, 2,5-dimethylfuran, 5-methylfurfural, protoanemonin and the like, which are contained as very small trace impurities other than organic acids in methyl methacrylate. In addition, it is impossible to remove said small trace impurities substantially by the conventional purification method. It has rarely been necessary to remove said very small trace impurities since, although they absorb visual rays having a relatively short wavelength, they do not absorb those having the other wavelengths. In specific uses such as materials for electronic parts, optical materials and the like, however, there is required highly purified methyl methacrylate from which even very small traces of impurities mentioned above have been removed.

The present inventors have found that the treatment of methyl methacrylate containing very small trace impurities, particularly traces of a furan type compound(s) with one or more sulfonic acid group-containing compounds produces the methyl methacrylate containing no trace of the impurities mentioned above.

An object of the present invention is to provide a process for purifying methyl methacrylate whereby very small traces of impurities such as furfural, 2,5-dimethylfuran, 5-methylfurfural, protoanemonin and the like can be easily and economically removed.

Another object of the present invention is to provide highly purified methyl methacrylate.

Other objects and advantages of the present invention will become apparent from the following description.

According to the present invention, there is provided a process for purifying methyl methacrylate which comprises treating the MMA with one or more sulfonic acid group-containing compounds, particularly a sulfonic acid group-containing ion exchange resin and, subjecting said treated liquid to distillation.

According to the present invention, there is, further, provided a methyl methacrylate monomer which exhibits a much smaller absorbance as measured according to the sulfuric acid color method than known methyl methacrylate monomers.

The sulfonic acid group-containing compound used in the present invention implies an inorganic or organic compound having a sulfonic acid group(s) in its molecule and specifically includes sulfuric acid, benzene sulfonic acid, p-toluene sulfonic acid and a strongly acidic cation exchange resin having sulfonic acid group as exchange group. They can be used alone or in combination. Particularly, a strongly acidic cation exchange resin is preferred.

The methyl methacrylate (the MMA) to be purified in the present invention has a purity of 99.5% or more. Preferably, the MMA has a purity of 99.7% or more in order to obtain methyl methacrylate of an ultra-high purity for optical fibers and the like.

As a process for producing methyl methacrylate, acetone cyanhydrin method or the catalytic oxidation method using isobutylene or tert-butanol as a starting material have been commercially adopted. Even if, however, the methyl methacrylate produced by the above-mentioned methods is purified by the conventional purification method, the recovered methyl methacrylate still contains 1–30 ppm of impurities such as furfural, 2,5-dimethylfuran, 5-methylfurfural, protoanemonin and the like. This methyl methacrylate is colored by the treatment according to the sulfuric acid color method and thereby usually exhibits an absorbance of 0.08 or more and, in a special case, 0.04–0.05, in a range of wavelength of 400–500 nm. This is because the boiling point of each of the impurities existing in the methyl methacrylate is close to that of methyl methacrylate itself and, hence, it is impossible to remove the impurities completely by distillation or the like.

The sulfuric acid color method is a colorimetric analysis comprising adding concentrated sulfuric acid having a purity of 98% or more to methyl methacrylate having a purity of 99.5% or more in a proportion of 5 ml for 50 ml of the methyl methacrylate, shaking the obtained mixture at a temperature of 25° C. for 30 minutes, charging the mixture into a cylinder-shaped glass cell having a cell thickness of 50 mm and thereafter measuring the absorption spectrum of the mixture using water as a blank.

For specific uses of methyl methacrylate, however, the conventional purity of methyl methacrylate is insufficient and therefore it is required to remove impurities such as furan-type compounds and the like almost completely from the methyl methacrylate. In such a case, the process of the present invention is effective.

According to the present invention, the MMA is purified by adding a proper amount of a sulfonic acid group-containing compound thereto and allowing the resulting mixture to stand for a given period optionally with heating and preferably with stirring the resulting mixture. In this case, the MMA is treated with 0.001–2 kg of a sulfonic acid group-containing compound per kg of methyl methacrylate at a temperature of 20°–70° C., preferably 40°–60° C. for preferably 1 min–2 hours, more preferably 5 min–20 min.

Also, according to the present invention, the MMA is purified by treating it with a sulfonic acid group-containing compound through a column filled with the same. For example, the MMA is purified by passing, at a constant running fluid speed, through a column filled with a strongly acidic cation exchange resin having sulfonic acid group as exchange group and, if necessary, heated. In this case, a proper space velocity (hereinafter referred to as SV) is selected in order to treat the MMA continuously and achieve a proper treatment efficiency. The SV is a ratio of the effluent volume per hour to the total volume of the ion exchange resin.

In the treatment of the MMA at a temperature of 40°–60° C., for example, an SV is selected in a range of 0.1– about 10 in order to secure a sufficient purity.

When the furan-type compound contained in the MMA contacts with one or more sulfonic acid group-containing compounds, the furan-type compound is converted into a compound having a higher boiling point (hereinafter referred to as the high boiling point compound) by the cleavage of the furan ring. The high boiling point compound is greatly different in boiling point from methyl methacrylate and therefore can be removed easily by ordinary distillation.

When the absorbance of the methyl methacrylate treated with one or more sulfonic acid group-containing compounds and thereafter distilled is measured in a range of wavelength of 400–500 nm according to the sulfuric acid color method, it results in an absorbance of 0.02 or less.

There has not been known heretofore a methyl methacrylate monomer which exhibits such a small absorbance in the range of wavelengths of the visual rays having short wavelengths.

A polymerization inhibitor such as phenothiazine, benzophenothiazine and the like is preferably added to the MMA prior to the treatment with one or more sulfonic acid group-containing compounds when the treatment is followed by the distillation, and thereafter, the treatment and the distillation are carried out in the existence of the polymerization inhibitor. The polymerization inhibitor exerts no bad influence upon the treatment and the distillation.

The present invention will be explained more specifically below referring to Examples. The present invention, however, should not be construed to be restricted to the Examples.

EXAMPLE 1

A strongly acidic cation exchange resin (a polystyrene resin DIAION PK-216 made by Mitsubishi Chemical Industries Ltd.) having -SO$_3$H as ion exchange group was previously dehydrated with absolute methanol. Further, the methanol was removed from the strongly acidic cation exchange resin with industrially rectified methyl methacrylate.

Methyl methacrylate having a purity of 99.8% or more containing, as trace impurities, 29 ppm of 2,5-dimethylfuran and 5 ppm of furfural was made to pass, at a SV of 2 and a temperature of 40° C., through a column packed with the strongly acidic cation exchange resin treated as above.

The content of each of the 2,5-dimethylfuran and furfural in the effluent was determined by a gas chromatograph with a hydrogen flame ionization detector. The contents were less than 1 ppm each which was the sensitivity limit of the gas chromatograph.

EXAMPLES 2–6

A process for purifying methyl methacrylate was carried out in the same manner as in Example 1, except that SV and treatment temperature were varied as shown in Table 1. The treated methyl methacrylate was subjected to simple distillation under reduced pressure. A distillate was collected at a temperature of 60° C. and a pressure of 35 mmHg. The content of each of the impurities contained therein was determined. Results are shown in Table 1.

EXAMPLE 7

Into a three neck flask with a 1-liter volume were charged 500 g of methyl methacrylate having a purity of 99.8% or more containing 29 ppm of 2,5-dimethylfuran, ppm of furfural, 5 ppm of protoanemonin and 10 ppm of -methylfurfural as trace impurities and 300 ppm of phenothiazine as a polymerization inhibitor.

To the resulting mixture was added 5 g of concentrated sulfuric acid having a purity of 98% or more. The three neck flask was equipped with a condenser. The resulting mixture was stirred at a temperature of 50° C. for 10 minutes and subjected to simple distillation under reduced pressure. A distillate was collected at a temperature of 50° C. and a pressure of 30 mmHg. The content of each of the impurities contained therein was determined by a gas chromatograph with a hydrogen flame ionization detector.

The contents of 2,5-dimethylfuran, furfural, protoanemonin and 5-methylfurfural were each 1 ppm or less. The absorbance measured according to the sulfuric acid color method was 0.01 or less.

EXAMPLE 8

A process for purifying methyl methacrylate was carried out in the same manner as in Example 2, except that the methyl methacrylate contained 1 ppm of 2,5-dimethylfuran as a trace impurity. The absorbance of the methyl methacrylate measured according to the sulfuric acid color method before the purification was 0.2–0.3 whereas that after the purification was 0.01 or less. Hence, the obtained methyl methacrylate proved to have a very high purity. Since the sensitivity limit of the gas chromatograph with a hydrogen flame ionization detector was about 1 ppm, the content of 2,5-dimethylfuran was considered to be less than 1 ppm from the determination according to the gas chromatography. It is, however, inferred from the absorbance that the content was in fact 1/20 ppm or less.

TABLE 1

|  |  | Treatment conditions | | Impurities (ppm) | |  |
| --- | --- | --- | --- | --- | --- | --- |
|  |  | Temperature (°C.) | SV | 2,5-Dimethylfuran | Furfural | Absorbance |
| Before treatment |  | — | — | 29 | 5 | More than 1.0 |
| Example | 2 | 40 | 4 | Less than 1 | Less than 1 | Less than 0.01 |
|  | 3 | " | 10 | Less than 1 | Less than 1 | Less than 0.01 |
|  | 4 | 50 | 2 | Less than 1 | Less than 1 | Less than 0.01 |
|  | 5 | " | 4 | Less than 1 | Less than 1 | Less than 0.01 |
|  | 6 | " | 10 | Less than 1 | Less than 1 | Less than 0.01 |

What is claimed is:

1. A process for purifying methyl methacrylate which comprises treating methyl methacrylate having a purity of 99.5% or more containing a trace of furan-type impurities with one or more sulfonic acid group-containing compounds.

2. A process for purifying methyl methacrylate which comprises treating methyl methacrylate having a purity of 99.7% or more containing a trace of impurities with one or more sulfonic acid group-containing compounds and then distilling the resulting treated liquid.

3. A process for purifying methyl methacrylate consisting essentially of treating methyl methacrylate having a purity of 99.5% or more containing a trace of a furan-type compound as an impurity with a sulfonic acid group-containing compound through a column filled with the same and then distilling the resulting treated liquid.

4. A process for purifying methyl methacrylate consisting essentially of treating methyl methacrylate having a purity of 99.5% or more containing a trace of a furan-type compound as an impurity with one or more sulfonic acid group-containing compounds which are liquid and then distilling the resulting treated liquid.

5. A process for purifying methyl methacrylate according to claim 3, wherein the furan-type compound is 2,5-dimethylfuran.

6. A process for purifying methyl methacrylate according to claim 1, wherein the sulfonic acid group-containing compound is a strongly acidic cation exchange resin having a sulfonic acid group as an exchange group.

7. A process for purifying methyl methacrylate according to claim 1, wherein the sulfonic acid group-containing compound is concentrated sulfuric acid having a purity of 98% or more.

8. A process for purifying methyl methacrylate according to claim 3, wherein the methyl methacrylate is treated at an SV of 0.1–10 and a temperature of 40°–60° C.

9. A process for purifying methyl methacrylate according to claim 7 wherein the concentrated sulfuric acid is added in a proportion of 0.01–2 kg per kg of the methyl methacrylate and the methyl methacrylate is treated with the concentrated sulfuric acid at a temperature of 20°–70° C. for 1 minute–2 hours.

10. A process for purifying methyl methacrylate according to claim 1, comprising further adding a polymerization inhibitor to the methyl methacrylate prior to the treatment.

11. A process for purifying methyl methacrylate according to claim 10, wherein the polymerization inhibitor is phenothiazine or benzophenothiazine.

12. A process for purifying methyl methacrylate according to claim 3, wherein the distilled liquid is methyl methacrylate exhibiting an absorbance of 0.02 or less in a range of wavelength of 400–500 nm according to the sulfuric acid color method, wherein the sulfuric acid color method is a colorimetric analysis comprising adding concentrated sulfuric acid having purity of 98% or more to methyl methacrylate in a proportion of 5 ml for 50 ml of the methyl methacrylate, shaking the resulting mixture at a temperature of 25° C. for 30 minutes and thereafter charging said mixture into a cylinder-shaped absorption cell having a cell thickness of 50 nm to measure the absorption spectrum of said liquid using water as a blank.

13. A process for purifying methyl methacrylate according to claim 4, wherein the distilled liquid is methyl methacrylate exhibiting an absorbance of 0.02 or less in a range of wavelength of 400–500 nm according to the sulfuric acid color method, wherein the sulfuric acid color method is a colorimetric analysis comprising adding concentrated sulfuric acid having purity of 98% or more to methyl methacrylate in a proportion of 5 ml for 50 ml of the methyl methacrylate, shaking the resulting mixture at a temperature of 25° C. for 30 minutes and thereafter charging said mixture into a cylinder-shaped absorption cell having a cell thickness of 50 nm to measure the absorption spectrum of said liquid using water as a blank.

* * * * *